(12) United States Patent
Chaudhary et al.

(10) Patent No.: US 9,481,633 B2
(45) Date of Patent: Nov. 1, 2016

(54) ACETYLATED POLYGLYCERINE FATTY ACID ESTER AND A PVC INSULATOR PLASTICISED THEREWITH

(75) Inventors: Bharat I. Chaudhary, Princeton, NJ (US); Beate Sczekalla, Halle (DE); Klaus Schiller, Halle (DE); Michael Meerbote, Gutenberg (DE)

(73) Assignee: Dow Global Technologies LLC, Midland, MI (US)

( * ) Notice: Subject to any disclaimer, the term of this patent is extended or adjusted under 35 U.S.C. 154(b) by 371 days.

(21) Appl. No.: 13/498,485

(22) PCT Filed: Sep. 29, 2010

(86) PCT No.: PCT/US2010/050664
§ 371 (c)(1),
(2), (4) Date: Mar. 27, 2012

(87) PCT Pub. No.: WO2011/041372
PCT Pub. Date: Apr. 7, 2011

(65) Prior Publication Data
US 2012/0181056 A1      Jul. 19, 2012

Related U.S. Application Data

(60) Provisional application No. 61/247,329, filed on Sep. 30, 2009.

(51) Int. Cl.
| | |
|---|---|
| *B32B 9/04* | (2006.01) |
| *C09K 3/00* | (2006.01) |
| *C07C 59/215* | (2006.01) |
| *C08K 5/11* | (2006.01) |
| *C07C 69/675* | (2006.01) |
| *C07C 69/33* | (2006.01) |
| *C08K 5/103* | (2006.01) |
| *C08K 5/1515* | (2006.01) |
| *H01B 3/44* | (2006.01) |

(52) U.S. Cl.
CPC ............ *C07C 69/675* (2013.01); *C07C 69/33* (2013.01); *C08K 5/103* (2013.01); *C08K 5/1515* (2013.01); *H01B 3/443* (2013.01)

(58) Field of Classification Search
None
See application file for complete search history.

(56) References Cited

U.S. PATENT DOCUMENTS

| | | | |
|---|---|---|---|
| 2,397,592 A | 4/1946 | Blades | |
| 4,083,816 A * | 4/1978 | Frankel et al. | 524/313 |
| 4,584,241 A | 4/1986 | Choi et al. | |
| 4,806,425 A * | 2/1989 | Chu-Ba | 428/379 |
| 4,857,600 A | 8/1989 | Gross et al. | |
| 5,575,965 A | 11/1996 | Caronia et al. | |
| 5,756,570 A * | 5/1998 | Hoch | C08K 3/0033 524/318 |
| 6,344,509 B1 * | 2/2002 | Mizutani | 524/322 |
| 6,479,607 B1 * | 11/2002 | Milan et al. | 526/317.1 |
| 2003/0079903 A1 * | 5/2003 | Scheidecker et al. | 174/110 F |
| 2005/0049341 A1 * | 3/2005 | Grass et al. | 524/306 |
| 2006/0276575 A1 | 12/2006 | Hamaguchi et al. | |
| 2007/0104701 A1 * | 5/2007 | Ueda et al. | 424/94.1 |
| 2007/0116909 A1 * | 5/2007 | Tweed et al. | 428/34.9 |
| 2008/0102272 A1 | 5/2008 | Sakamoto et al. | |
| 2008/0179417 A1 * | 7/2008 | Bayer et al. | 238/84 |
| 2010/0298477 A1 * | 11/2010 | Godwin | 524/285 |

FOREIGN PATENT DOCUMENTS

| | | |
|---|---|---|
| CN | 1696835 A | 11/2005 |
| CN | 1829768 A | 9/2006 |
| GB | 0531023 | 3/1993 |
| GB | 1728818 | 12/2006 |
| JP | H11-349765 A | 12/1999 |
| JP | 2000-327870 A | 11/2000 |
| JP | 2002-226689 A | 8/2001 |
| JP | 2002-178473 A | 6/2002 |
| JP | 2004359892 * | 12/2004 |
| JP | 2005-336305 A | 12/2005 |
| WO | 0020296 A1 | 4/2000 |
| WO | 01/14466 A1 | 3/2001 |
| WO | 2009118261 | 10/2009 |

OTHER PUBLICATIONS

Asian and Pacific Coconut Community, The Plain Truth about Coconut Oil, Jun. 18, 2003.*
Scientific Psychic—Fats, Oils, Fatty Acids, Triglycerides. Aug. 31, 2008.*
Elmhurst College, Virtual Chembook—Triglyceride. Retrieved on Mar. 10, 2014.*
Nakamura et al., JP2004359892 machine translation. Dec. 24, 2004.*
ChemSpider: Lauric acid. Retrieved on Sep. 8, 2014.*
ChemSpider: 12-hydroxystearic acid. Retrieved on Sep. 9, 2014.*
Parzuchowski et al., New hyperbranched polyether containing cyclic carbonate groups as a toughening agent for epoxy resinPolymer, vol. 48, Issue 7, Mar. 23, 2007, pp. 1857-1865.*
Belden, Cable 101—The basic of Wire & Cable. 2007 https://www.belden.com/docs/upload/Insulations-Jackets.pdf.*
Telephone & Communication Cable, 2007. http://alliedcables.net/telephone_and_communication.cable.php.*
Machine translation of CN 1829768, Sep. 6, 2006.
Machine translation of CN 1696835, Nov. 16, 2005.

* cited by examiner

*Primary Examiner* — Coris Fung
(74) *Attorney, Agent, or Firm* — Husch Blackwell LLP

(57) ABSTRACT

The present disclosure is directed to acetylated polyglyceride fatty acid ester and compositions containing the same. The acetylated polyglyceride fatty acid ester may be blended with an epoxidized fatty acid ester. The present acetylated polyglyceride fatty acid ester and blends find advantageous application as a plasticizer.

16 Claims, No Drawings

ACETYLATED POLYGLYCERINE FATTY ACID ESTER AND A PVC INSULATOR PLASTICISED THEREWITH

PRIORITY

This application claims priority to U.S. patent application No. 61/247,329, filed on Sep. 30, 2009, the entire content of which is incorporated by reference herein.

BACKGROUND

Plasticizers are compounds or mixtures of compounds that are added to polymer resins to impart softness and flexibility. Phthalic acid diesters (also known as "phthalates") are known plasticizers in many flexible polymer products, such as polymer products formed from polyvinyl chloride (PVC) and other vinyl polymers. Examples of common phthalate plasticizers include, di-isononyl phthalate (DINP), diallyl phthalate (DAP), and di-2-ethylhexyl-phthalate (DEHP), dioctyl phthalate (DOP) and diisodecyl phthalate (DIDP). Other common plasticizers, used for high temperature applications, are trimellitates and adipic polyesters. Mixtures of plasticizers are often used to obtain optimum properties.

Phthalate plasticizers have recently come under intense scrutiny by public interest groups that are concerned about the negative environmental impact of phthalates and potential adverse health effects in humans (especially children) exposed to phthalates.

Consequently, a need exists for phthalate-free plasticizers for polymer resins. A need further exists for phthalate-free plasticized polymers that have the same, or substantially the same, chemical, mechanical, and/or physical properties as polymers containing phthalate plasticizers.

SUMMARY

The present disclosure is directed to acetylated polyglyceride fatty acid esters and compositions containing the same. A nonlimiting beneficial application for the acetylated polyglyceride fatty acid ester is as a plasticizer.

In an embodiment, an acetylated polyglyceride fatty acid ester is provided. The acetylated fatty acid ester includes a polyglyceride with at least one fatty acid component having from about 4 to about 22 carbon atoms. The acetylated polyglyceride fatty acid ester also includes at least one acetyl group.

The present disclosure provides a composition including one, two, three, or more plasticizers. In an embodiment, the composition includes a first plasticizer and optionally a second plasticizer. The first plasticizer includes an acetylated fatty acid ester.

In an embodiment, a polymeric composition is provided. The polymeric composition includes a polymeric resin and a plasticizer composition. The plasticizer composition includes an acetylated polyglyceride fatty acid ester and optionally other plasticizers including, but not limited to, an epoxidized fatty acid ester.

In an embodiment, a coated conductor is provided. The coated conductor includes a conductor and a coating on the conductor. The coating includes a polymeric resin and a plasticizer composition containing one, two, three, or more plasticizers. The plasticizer composition includes an acetylated polyglyceride fatty acid ester and optionally other plasticizers including, but not limited to, an epoxidized fatty acid ester.

An advantage of the present disclosure is an environmentally safe plasticizer for polymer resins.

An advantage of the present disclosure is a phthalate-free plasticizer with low, or no, adverse health risk to humans.

An advantage of the present disclosure is a phthalate-free plasticizer which provides the same, or substantially the same, properties to a polymer resin as the same polymer resin containing a phthalate-containing plasticizer.

An advantage of the present disclosure is a coating for wire and cable that is phthalate-free.

DETAILED DESCRIPTION

The present disclosure is directed to acetylated polyglyceride fatty acid esters and compositions including the same. The compositions provided herein are suitable for use as plasticizers in polymer resins and vinyl chloride resins in particular.

All references to the Periodic Table of the Elements refer to the Periodic Table of the Elements published and copyrighted by CRC Press, Inc., 2003. Also, any references to a Group or Groups shall be to the Group or Groups reflected in this Periodic Table of the Elements using the IUPAC system for numbering groups. Unless stated to the contrary, implicit from the context, or customary in the art, all parts and percents are based on weight and all test methods are current as of the filing date of this disclosure. For purposes of United States patent practice, the contents of any referenced patent, patent application or publication are incorporated by reference in their entirety (or its equivalent U.S. version is so incorporated by reference) especially with respect to the disclosure of synthetic techniques, product and processing designs, polymers, catalysts, definitions (to the extent not inconsistent with any definitions specifically provided in this disclosure), and general knowledge in the art.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, melt index, etc., is from 100 to 1,000, then the intent is that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, the amounts for components in the thermoplastic composition and/or coating, additives, and various other components in the thermoplastic composition, and the various characteristics and properties by which these components are defined.

As used with respect to a chemical compound, unless specifically indicated otherwise, the singular includes all isomeric forms and vice versa (for example, "hexane", includes all isomers of hexane individually or collectively). The terms "compound" and "complex" are used interchangeably to refer to organic-, inorganic- and organometal compounds. The term, "atom" refers to the smallest constituent of an element regardless of ionic state, that is, whether or not the same bears a charge or partial charge or is bonded to another atom. The term "amorphous" refers to a polymer lacking a crystalline melting point as determined by differential scanning calorimetry (DSC) or equivalent technique.

The terms "comprising", "including", "having" and their derivatives are not intended to exclude the presence of any additional component, step or procedure, whether or not the same is specifically disclosed. In order to avoid any doubt, all compositions claimed through use of the term "comprising" may include any additional additive, adjuvant, or compound whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or", unless stated otherwise, refers to the listed members individually as well as in any combination.

"Composition" and like terms mean a mixture or blend of two or more components.

"Blend," "polymer blend" and like terms mean a blend of two or more polymers, as well as blends of polymers with various additives. Such a blend may or may not be miscible. Such a blend may or may not be phase separated. Such a blend may or may not contain one or more domain configurations, as determined from transmission electron spectroscopy, light scattering, x-ray scattering, and any other method known in the art.

The term "polymer" (and like terms) is a macromolecular compound prepared by reacting (i.e., polymerizing) monomers of the same or different type. "Polymer" includes homopolymers and copolymers.

In an embodiment, the compositions disclosed herein are phthalate-free. The term "phthalate-free composition," as used herein, is a composition devoid of phthalate or is otherwise free of phthalate. A "phthalate," is a compound which includes the following structure (I):

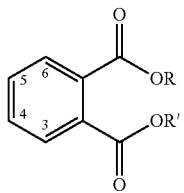

(I)

wherein R and R' may be the same or different. Each of R and R' is selected from a substituted-/unsubstituted-hydrocarbyl group having 1 to 20 carbon atoms. As used herein, the term "hydrocarbyl" and "hydrocarbon" refer to substituents containing only hydrogen and carbon atoms, including branched or unbranched, saturated or unsaturated, cyclic, polycyclic, fused, or acyclic species, and combinations thereof. Nonlimiting examples of hydrocarbyl groups include alkyl-, cycloalkyl-, alkenyl-, alkadienyl-, cycloalkenyl-, cycloalkadienyl-, aryl-, aralkyl, alkylaryl, and alkynyl- groups. Each position 3, 4, 5, and 6 may be populated by hydrogen or other moiety.

The present disclosure is directed to polyglyceride fatty acid esters and processes for producing the same. In an embodiment, a process for producing an acetylated polyglyceride fatty acid ester (or APE) is provided. The process includes forming a polyglyceride fatty acid ester. The polyglyceride fatty acid ester is subsequently acetylated to form an acetylated polyglyceride fatty acid ester. In an embodiment, the acetylated polyglyceride fatty acid esters disclosed herein are phthalate-free.

The process includes forming a polyglyceride fatty acid ester. The formation of polyglyceride fatty acid ester occurs by way of (i) esterification between a polyglycerol and a fatty acid or (ii) transesterification between a polyglycerol and a triglyceride. A "polyglycerol," as used herein, is a glycerol oligomer with two or more glycerol units linked by way of an ether bond. Nonlimiting reaction mechanisms for polyglycerol production include: (i) the reaction product of glycerol condensation; and (ii) the reaction between glycerol with epichlorohydrin. The degree of condensation determines the degree of polymerization, typically between 2 and 10.

Nonlimiting examples of suitable polyglycerols include diglycerol, triglycerol, tetraglycerol, pentaglycerol, hexaglycerol, heptaglycerol, octaglycerol, nonaglycerol, decaglycerol, and combinations thereof. In an embodiment, the degree of polymerization for the polyglycerol is from 3 to 5. In a further embodiment, the polyglycerol is tetraglycerol. The structure of the polyglycerol affects the properties of the final acetylated polyglyceride fatty acid ester as will be discussed in detail below. The polyglycerol product may contain significant amounts of free glycerol. Suitable polyglycerol products include Diglycerol (product of Solvay), Polyglycerol-3 (product of Solvay), Polyglycerol-4 (product of Solvay), R-PG Polyglycerol-3 (product of Sakamoto Yakuhin Kogyo), Polyglycerin #310 tetraglycerol (product of Sakamoto Yakuhin Kogyo), Polyglycerin #500 hexaglycerol (product of Sakamoto Yakuhin Kogyo) and Polyglycerin #750 decaglycerol (product of Sakamoto Yakuhin Kogyo).

A "fatty acid," as used herein, is a monocarboxylic acid composed of an aliphatic chain containing 4 to 22 carbon atoms with a terminal carboxyl group (COOH). The fatty acid can be saturated or unsaturated, branched or unbranched, and may or may not include one or more hydroxyl group(s). The term "fatty acid component" is the fatty acid moiety of the polyglyceride fatty acid ester after esterification.

In an embodiment, the fatty acid contains from 4 to 22 carbon atoms. Nonlimiting examples of suitable fatty acids include caprylic acid (C8), capric acid (C10), lauric acid (C12), myristic acid (C14), 12-hydroxystearic acid (C18), palm kernel oil acid (a mixture of C8-C22 fatty acids and primarily lauric acid and myristic acid), coconut oil acid (a mixture of C8-C22 fatty acids, primarily lauric acid and myristic acids), castor oil acid (predominantly ricinoleic acid), hydrogenated castor oil (predominantly hydrogenated ricinoleic acid), and any combination of the foregoing.

In an embodiment, the fatty acid is lauric acid.

In another embodiment, the fatty acid is 12-hydroxystearic acid.

A "triglyceride," as used herein, is a triester of a fatty acid and glycerol. Nonlimiting examples of triglycerides include vegetable and plant oils (coconut oil, corn oil, palm kernel oil, castor oil, hydrogenated castor oil), waxes, and fats.

The polyglyceride fatty acid ester can be formed by way of esterification between the polyglycerol and the fatty acid or by way of transesterification between the polyglycerol and the triglyceride. The esterification may or may not be catalyzed with an organometallic catalyst, such as tin octoate, for example. The transesterification may be catalyzed by an alkaline catalyst. The degree of esterification with respect to the fatty acid is from 0 to 12. The mole ratio of fatty acid to polyglycerol may be adjusted to produce mono-, di-, tri-, tetra-, penta-, hexa-, hepta-, octa-, nona-, deca-, monodeca- and/or dodeca-fatty acid esters of polyglyceride. In an embodiment, the degree of esterification with respect to the fatty acid is from 0.5 to 3. The "degree of esterification," as used herein, is the mole ratio of fatty acid to polyglycerol.

A schematic representation of esterification and transesterification of a tetraglycerol is provided in (II) below.

resins (such as vinyl chloride resins). Applicants have surprisingly discovered that acetylation of the polyglyceride fatty acid ester reduces hydrogen bonding within the polyglyceride fatty acid ester. Acetylation caps the —OH groups of the polyglycerol moiety and lowers the viscosity of the high MW fatty acid esterified polyglyceride by reducing the H-bonding. The reduction in viscosity yields a final acetylated polyglyceride fatty acid ester with a synergistic combination of (i) high molecular weight (reduced volatility) and (ii) low viscosity (low H-bonding). The present APE exhibits excellent compatibility when blended with polymer resins.

The unexpected synergy between the high molecular weight and low viscosity exhibited by the present APE,

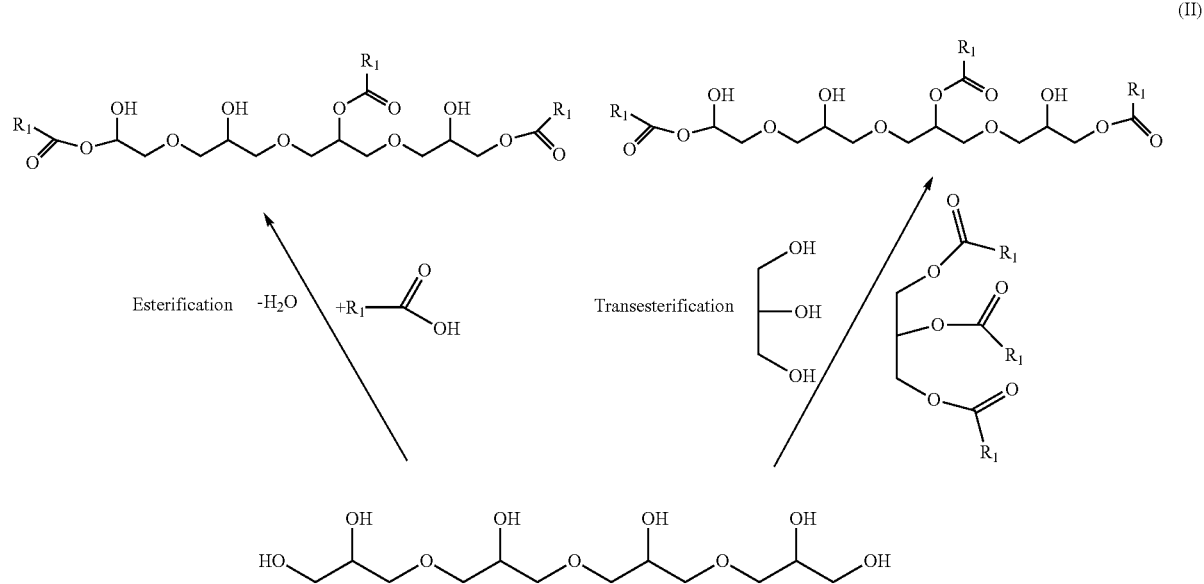

(II)

$R_1$ is a carbon chain containing 1 to 22 carbon atoms.

The present process includes acetylating the polyglyceride fatty acid ester to form the acetylated polyglyceride fatty acid ester. The term "acetylating" or "acetylation," as used herein, is the process of introducing an acetyl group into the molecule of a compound having —OH groups. In other words, acetylation replaces H of the —OH groups with $CH_3CO$— groups. Acetylation may also occur with the fatty acid component when the fatty acid component includes a hydroxyl group. Nonlimiting examples of suitable acetylation reagents include acetic anhydride and acetyl chloride. Some, substantially all, or all of the —OH groups of the polyglyceride fatty acid ester may be acetylated. An "acetylated polyglyceride fatty acid ester" (or APE) is a polyglyceride fatty acid ester in which one, some, substantially all, or all —OH groups are acetylated. In an embodiment, the acetylated polyglyceride fatty acid ester (APE) comprises one or more of acetylated mono-/di-/tri-/tetra-/penta-/hexa-/hepta-/octa-/nona-/deca-/monodeca-/dodeca-fatty acid esters of polyglyceride, acetylated monoglyceride of fatty acid, acetylated diglyceride of fatty acid, acetylated triglyceride of fatty acid, glycerol, polyglycerol, triacetin (glycerin triacetate), acetylated polyglycerol, and any combination thereof.

Polyglyceride fatty acid esters with high molecular weight ("MW") are typically incompatible with many polymer advantageously provides the APE with plasticizing properties when applied to polymer resins. In an embodiment, the APE has a molecular weight from about 500 to about 2000 g/mol and a viscosity from about 100 to about 3000 mPa s at 25° C. (measured with a Brookfield-Viscosimeter in accordance with ASTM D445).

In an embodiment, the process includes acetylating substantially all, or all, the —OH groups of the polyglyceride fatty acid ester. The acetylation results in an acetylated polyglyceride fatty acid ester having a hydroxyl number from 0 to less than 450, or from 0 to less than 200, or from 0 to less than 100, or from 0 to less than 50, or from 0 to less than 15, or from 0 to less than 10, or from 0 to less than 5, or from 0 to less than 2, or 0. Capping the hydroxyl groups advantageously lowers the viscosity of the APE as discussed above.

In an embodiment, the acetylated polyglyceride fatty acid ester has an acid number from about 0 mg KOH/g to about 8 mg KOH/g. The acid value is determined in accordance with DIN 53402.

In an embodiment, the acetylated polyglyceride fatty acid ester has an APHA color from about 0 to about 3000, or from about 0 to about 1000, or from about 0 to about 500.

In an embodiment, the process includes reacting, or otherwise esterifying, polyglycerol with a fatty acid, subsequently acetylating the fatty acid ester intermediate, and forming an acetylated polyglyceride fatty acid ester based on a polyglycerol with an average degree of polymerization from about 3 to about 5.

In an embodiment, the process includes esterifying tetraglycerol with a fatty acid selected from lauric acid, 12-hydroxystearic acid, and combinations thereof.

In an embodiment, the process includes transesterifying tetraglycerol with palm kernel oil, coconut oil, castor oil, castor wax (hydrogenated castor oil), and combinations thereof. The fatty acid ester intermediate is subsequently acetylated to form an acetylated polyglyceride fatty acid ester.

The present process may comprise two or more embodiments disclosed herein.

The present disclosure is also directed to the acetylated polyglyceride fatty acid ester produced by the foregoing process(es). In an embodiment, an acetylated polyglyceride fatty acid ester (APE) is provided which includes a polyglyceride moiety and at least one fatty acid component. The fatty acid component has from about 4 to about 22 carbon atoms. The APE also includes at least one acetyl group.

In an embodiment, the APE includes at least three acetyl groups.

In an embodiment, the APE has a hydroxyl number from 0 to less than 450, or from 0 to less than 200, or from 0 to less than 100, or from 0 to less than 50, or from 0 to less than 15, or from 0 to less than 10, or from 0 to less than 5, or from 0 to less than 2, or 0.

In an embodiment, the APE has a viscosity from about 100 to about 3000 mPa s at 25° C. and a molecular weight from about 500 to about 2000 g/mol.

In an embodiment, the polyglyceride moiety is derived from a polyglycerol with an average degree of polymerization from 3 to 5. In a further embodiment, the polyglycerol moiety is tetraglycerol.

In an embodiment, the fatty acid ester component of the APE is lauric acid.

In an embodiment, the fatty acid ester component of the APE is 12-hydroxystearic acid.

The APE may comprise two or more embodiments disclosed herein.

The APE may contain significant amount of insoluble component. The term "insoluble component," as used herein, is one or more compounds that phase separate out of the APE over time, especially when held at room temperature and below. The APE is a liquid at room temperature and the insoluble component may phase separate out of the liquid phase APE as a solid phase. The insoluble component turns the APE cloudy and settles to the bottom. The lower the temperature, the more insolubles are formed. Furthermore, the quality of raw materials (such as polyglycerol, fatty acid and triglyceride) used to make the polyglyceride fatty acid ester has an effect on the amount of insolubles formed after acetylation, as well as the color of the APE.

The APE may be subjected to a purification process to reduce the color and decrease the amount of insolubles. A "purification process," as used herein, is the application of one or more of the following procedures to the APE: a filtration procedure, a centrifugation procedure, a sedimentation procedure, treatment with additives [such as silicon dioxide ($SiO_2$), aluminum oxide ($Al_2O_3$), activated carbon, Perlite (naturally occurring amorphous siliceous volcanic rock), diatomaceous earth) and combinations thereof. Any of these procedures may optionally be performed at a temperature from 5° C. to 50° C. and holding at this temperature for at least 3 hours. The additives may be used to aid the filtration step and may also result in desirably lighter color of the APE. The purification process removes, wholly or partially, any insoluble components present in the APE and can also result in desirably lighter color. Treatment of the APE with additives, followed by filtration, can also be performed at temperatures as high as 150° C. to result in lighter color, without necessarily decreasing the amount of insolubles. With removal of the solid phase from the APE and/or lighter color, the resultant filtrate from the purification process is clear and has low, or no, turbidity. A "purified APE" is an APE that has been subjected to at least one of the foregoing purification processes and exhibits at least one of the following properties: lighter color, fewer (or no) insoluble components, and/or less (or no) turbidity compared to the APE prior to purification.

The present disclosure provides a composition containing one, two, three, or more plasticizers. In an embodiment, a composition (or a plasticizer composition) is provided and includes a blend of (i) a first plasticizer including the APE and optionally (ii) a second plasticizer. In an embodiment, the composition includes a blend of (i) the APE and (ii) a second plasticizer which includes an epoxidized fatty acid ester (EFA). The APE may be any APE previously disclosed herein with no limit regarding hydroxyl number and/or viscosity. The term "epoxidized fatty acid ester," as used herein, is a compound with at least one fatty acid moiety which contains at least one epoxide group. An "epoxide group" is a three-membered cyclic ether (also called oxirane or an alkylene oxide) in which an oxygen atom is joined to each of two carbon atoms that are already bonded to each other. Nonlimiting examples of suitable epoxidized fatty acid esters include epoxidized animal and vegetable oils, such as naturally occurring epoxidized oils, epoxidized soybean oil (ESO), epoxidized propylene glycol dioleate, epoxidized corn oil, epoxidized sunflower oil, epoxidized palm oil, epoxidized linseed oil, epoxidized canola oil, epoxidized rapeseed oil, epoxidized safflower oil, epoxidized tall oil, epoxidized tung oil, epoxidized fish oil, epoxidized beef tallow oil, epoxidized castor oil, epoxidized methyl stearate, epoxidized butyl stearate, epoxidized 2-ethylhexyl stearate, epoxidized stearyl stearate, 3,4-epoxycyclohexylmethyl-3,4-epoxycyclohexane carboxylate epoxidized soybean oil, epoxidized fatty acid methyl esters, epoxidized derivatives of each of the foregoing, and any combination of the foregoing. A nonlimiting example of naturally occurring epoxidized oils is Vernonia oil.

The second plasticizer may also include epoxidized polybutadiene, tris(epoxypropyl)isocyanurate, bisphenol A diglycidyl ether, vinylcyclohexene diepoxide, dicyclohexene diepoxide and any combination thereof.

The epoxidized fatty acid ester can be prepared in a variety of ways. For example, natural oils can be used as the starting material. In this instance, the natural oils may be saponified to the fatty acids and then esterified with alcohols. Next, the low molecular weight esters are epoxidized. The unsaturated ester can be epoxidized with a per-acid. Alternatively, a glycidyl ester of the fatty acid can be prepared via epichlorohydrin or related chemicals. In yet another alternate, it is possible to transesterify the triglyceride with alcohols and then epoxidize the unsaturated fatty ester with a per-acid.

In an embodiment, the epoxidized fatty acid ester can be any epoxidized fatty acid $C_1$-$C_{14}$ ester, including methyl, ethyl, propyl, butyl, and 2-ethylhexyl esters. In a further embodiment, the epoxidized fatty acid ester is an epoxide of a fatty acid methyl ester.

A nonlimiting example for the preparation of an epoxide of a fatty acid methyl ester begins with soy oil, wherein the soy oil is transesterified with methanol to make the methyl ester of the fatty acids in the oil. Glycerol is removed from the reaction products due to insolubility. A solution of per-acetic acid in ethyl acetate is used to epoxidize the double bonds on the fatty acids. The per-acid is kept below 35% per-acid and 35 degrees Celsius to prevent detonation. After completion, the ethyl acetate and product acetic acid are removed via vacuum stripping.

In an embodiment, the epoxidized fatty acid ester is epoxidized soybean oil (ESO).

In an embodiment, the composition (or plasticizer composition) is an APE/EFA mixture. The APE/EFA mixture may be referred to as a "APE/EFA plasticizer". The APE/EFA plasticizer may include from about 1 wt % to about 100 wt %, or from about 10 wt % to about 90 wt % APE and from about 99 wt % to about 0 wt %, or from about 90 wt % to about 10 wt % EFA (based on the total weight of the plasticizer composition). In an embodiment, the APE/EFA mixture contains 87 wt % APE and 13 wt % EFA. In another embodiment, the APE/EFA mixture contains 50 wt % APE and 50 wt % EFA.

The APE is advantageously added to polymeric resins (and other materials) as a phthtalate-free plasticizer. A "plasticizer composition" or "plasticizer" is a substance that lowers the modulus and tensile strength, and increases flexibility, elongation, impact strength, and tear strength of the polymeric resin (typically a thermoplastic polymer) to which it is added. A plasticizer may also lower the melting point of the polymeric resin, lowering the glass transition temperature and enhancing processability of the polymeric resin to which it is added.

In an embodiment, the plasticizer composition includes an APE with a hydroxyl number from 0 to less than 450, or from 0 to less than 15, or from 0 to less than 10, or from 0 to less than 5, or from 0 to less than 2, or 0, and a viscosity from about 100 mPa s to about 3000 mPa s at 25° C. The APE may be blended with any of the foregoing EFAs.

In an embodiment, the plasticizer composition may include one or more APE and/or one or more EFA. In an embodiment, the plasticizer composition includes an APE having a hydroxyl number from 0 to less than 450, or from 0 to less than 15, or 0 to less than 10, or 0 to less than 5, or from 0 to less than 2, or 0, and epoxidized soybean oil (ESO). In a further embodiment, the APE of the plasticizer composition has a hydroxyl number of 0 and also includes ESO.

In an embodiment, the plasticizer composition includes an APE, a first EFA, and a second EFA. The second EFA is different than the first EFA. In a further embodiment, the plasticizer composition includes an APE, ESO, and an epoxidized propylene glycol dioleate. In yet another embodiment, the plasticizer composition includes an APE, ESO, and an epoxidized fatty acid methyl ester.

Although the composition of this disclosure may be phthalate-free, in an embodiment, the plasticizer composition may also comprise other plasticizers including, but not limited to, phthalates (such as di-isononyl phthalate, diallyl phthalate, di-2-ethylhexyl-phthalate, dioctyl phthalate, diisodecyl phthalate and diisotridecyl phthalate), trimellitates (such as trioctyl trimellitate, triisononyl trimellitate and triisodecyl trimellitate), citrates, Grindsted® Soft-N-Safe acetylated monoglyceride of hydrogenated castor oil (product of Danisco), Hexamoll® DINCH diisononyl ester of 1,2-Cyclohexanedicarboxylic acid (product of BASF), benzoates and adipic polyesters.

The present composition may comprise two or more embodiments disclosed herein.

The present composition composed of APE alone or in combination with any EFA and/or other plasticizers may be used in a variety of compositions or products. Nonlimiting examples of suitable applications for the composition include cosmetic compositions/products, food compositions/products, and polymeric compositions/products, soft thermoplastic polyolefins, profiles (gaskets), films, etc.

The present disclosure provides a polymeric composition. In an embodiment, a polymeric composition is provided which includes a polymeric resin and a plasticizer composition containing one, two, three, or more plasticizers. The plasticizer composition may be any composition previously described herein. In an embodiment, the plasticizer composition includes a first plasticizer (APE) alone or in combination with a second plasticizer such as any EFA as disclosed herein. The polymeric composition contains from about 1 wt % to about 99 wt % of the polymeric resin and from about 99 wt % to about 1 wt % of the plasticizer composition. Weight percent is based on total weight of the polymeric composition.

Nonlimiting examples of suitable polymeric resins include polysulfides, polyurethanes, acrylics, epichlorohydrins, nitrile rubber, chlorosulfonated polyethylene, chlorinated polyethylene, polychloroprene, styrene butadiene rubber, natural rubber, synthetic rubber, EPDM rubber, propylene-based polymers, ethylene-based polymers, and vinyl chloride resins. The term, "propylene-based polymer," as used herein, is a polymer that comprises a majority weight percent polymerized propylene monomer (based on the total amount of polymerizable monomers), and optionally may comprise at least one polymerized comonomer. The term, "ethylene-based polymer," as used herein, is a polymer that comprises a majority weight percent polymerized ethylene monomer (based on the total weight of polymerizable monomers), and optionally may comprise at least one polymerized comonomer.

The term "vinyl chloride resin," as used herein, is a vinyl chloride polymer, such as polyvinyl chloride (PVC), or a vinyl chloride copolymer such as vinyl chloride/vinyl acetate copolymer, vinyl chloride/vinylidene chloride copolymer, vinyl chloride/ethylene copolymer or a copolymer prepared by grafting vinyl chloride onto ethylene/vinyl acetate copolymer. The resin composition can also include a polymer blend of the above-mentioned vinyl chloride polymer or vinyl chloride copolymer with other miscible or compatible polymers including, but not limited to, chlorinated polyethylene, thermoplastic polyurethane, olefin polymers such as a methacryl polymer or acrylonitrile-butadiene-styrene polymer (ABS resin).

In an embodiment, the vinyl chloride resin is polyvinyl chloride (PVC).

In an embodiment, the polymeric composition is a thermoplastic composition. A "thermoplastic composition," as used herein, is a polymeric composition (1) that has the ability to be stretched beyond its original length and retract to substantially its original length when released and (2) softens when exposed to heat and returns to substantially its original condition when cooled to room temperature.

In an embodiment, the polymeric composition includes the polymeric resin and a plasticizer composition including one or more APE, optionally a first EFA, and optionally a second EFA.

In an embodiment, the polymeric composition includes PVC, an APE and optionally an EFA. The polymeric composition has a Shore hardness from about A60 to about A100, or from about A70 to about A95. In an embodiment, the polymeric composition has a Shore hardness from about D10 to about D70, or from about D20 to about D60.

In an embodiment, the plasticizer composition has a solution temperature from about 140° C. to about 200° C., or from about 150° C. to about 190° C. as measured in accordance with DIN 53408. Applicants have surprisingly discovered that the plasticizer composition composed of APE and optionally EFA unexpectedly provides a plasticizer with low viscosity and low volatility, which is particularly suitable for high temperature wire and cable applications, and which does not migrate out of a thermoplastic polymer in which it is incorporated. In addition, the solution temperature (of 140° C.-200° C.) for the present plasticizer composition is similar to the solution temperature of conventional high molecular weight plasticizers (typically between about 140° C. and about 180° C.). Moreover, the viscosity of the present plasticizer composition is less than the viscosity of conventional high molecular weight plasticizers, such as adipic polyester plasticizers. For example, adipic polyester plasticizers, known commercially as Ultramoll® IV and Ultramoll® III adipic polyesters (products of Lanxess) have very high viscosity (approximately 6000 to 6500 mPa at 25° C.). It is known that the lower the viscosity of a plasticizer, the faster is its uptake into PVC powder. Hence, the present plasticizers compositions, e.g., APE (hydroxyl number from 0 to less than 450) with viscosity from about 100 mPa s to about 3000 mPa s (at 25° C.) alone or in combination with one or more EFA, are absorbed into PVC at a faster rate than adipic polyester plasticizers, and even trimellitates of lower or similar viscosity. The present plasticizer composition exhibits an unexpected synergy between low viscosity and high molecular weight and yields a phthalate-free, safe, plasticized PVC with physical, chemical, and mechanical properties that meet and/or exceed the properties of PVC resins plasticized with conventional adipic polyester plasticizers and/or conventional phthalate-based plasticizers and/or conventional trimellitate-based plasticizers. Especially noteworthy is the retention of tensile properties exhibited by the present composition after oven aging for 168 hours at temperatures as high as 136° C. Even more especially noteworthy is the retention of tensile properties exhibited by the present composition after oven aging for 96 hours in IRM 902 oil at temperatures as high as 100° C.

The present polymeric composition exhibits the same, or better, flexibility and/or elongation when compared to polymer resins containing conventional adipic polyester, phthalate, and/or trimellitate plasticizers. In an embodiment, the present composition is a blend of PVC and an APE/EFA plasticizer and has a Shore hardness from about A60 to about A100, or from about A70 to about A95. In an embodiment, the present polymeric composition has a Shore hardness from about D10 to about D70, or from about D20 to about D60. Shore hardness is measured in accordance with ASTM D2240.

In an embodiment, the polymeric composition is a blend of PVC and APE/EFA plasticizer and has a glass transition temperature ("Tg") from about 10° C. to about 90° C., or from about 20° C. to about 80° C., or from about 25° C. to about 75° C.

In an embodiment, the polymeric composition is composed of a blend of PVC and the APE/EFA plasticizer. The polymeric composition is molded into a plaque. The plaque has a tensile strength retention greater than about 70% after 168 hours heat aging at 113° C. or 136° C. as measured on dogbones cut from 30 mil thick plaques in accordance with ASTM D638.

In an embodiment, the polymeric composition is composed of a blend of PVC and the APE/EFA plasticizer. The polymeric composition is molded into a plaque. The plaque has a tensile strength retention greater than about 70% after 96 hours heat aging at 100° C. in IRM 902 oil as measured on dogbones cut from 30 mil thick plaques in accordance with ASTM D638.

In an embodiment, the polymeric composition is composed of a blend of PVC and the APE/EFA plasticizer. The polymeric composition is molded into a plaque. The plaque has a tensile elongation retention greater than about 30% after 168 hours heat aging at 113° C. as measured on dogbones cut from 30 mil thick plaques in accordance with ASTM D638.

In an embodiment, the polymeric composition is composed of a blend of PVC and the APE/EFA plasticizer. The polymeric composition is molded into a plaque. The plaque has a tensile elongation retention greater than about 30% after 168 hours heat aging at 136° C. as measured on dogbones cut from 30 mil thick plaques in accordance with ASTM D638.

In an embodiment, the polymeric composition is composed of a blend of PVC and the APE/EFA plasticizer. The polymeric composition is molded into a plaque. The plaque has a tensile elongation retention greater than about 30% after 96 hours heat aging at 100° C. in IRM 902 oil as measured on dogbones cut from 30 mil thick plaques in accordance with ASTM D638.

The tensile strength and tensile elongation is measured for (i) unaged and (ii) heat aged and (iii) oil aged dogbone specimens cut from compression molded plaques in accordance with ASTM D-638.

Any of the foregoing polymeric compositions may include one or more of the following additives: a filler, an antioxidant, a flame retardant (antimony trioxide, molybdic oxide and alumina hydrate), a heat stabilizer, an anti-drip agent, a colorant, a lubricant, a low molecular weight polyethylene, a hindered amine light stabilizer (having at least one secondary or tertiary amine group) ("HALS"), UV light absorbers (such as o-hydroxyphenyltriazines), curing agents, boosters and retardants, processing aids, coupling agents, antistatic agents, nucleating agents, slip agents, viscosity control agents, tackifiers, anti-blocking agents, surfactants, extender oils, acid scavengers, metal deactivators, and any combination thereof.

In an embodiment, the polymeric composition includes a filler. Nonlimiting examples of suitable fillers include calcium carbonate, calcined clay, whiting, fuller's earth, magnesium silicate, barium sulfate, calcium sulfate, strontium sulfate, titanium dioxide, magnesium oxide, magnesium hydroxide, calcium hydroxide, hydrophilic fumed silica, hydrophobic (surface treated) fumed silica, and any combination of the foregoing. Nonlimiting examples of calcined clay are Satintone® SP-33 and Polyfil® 70.

In an embodiment, the polymeric composition includes an antioxidant. Nonlimiting examples of suitable antioxidants include hindered phenols such as tetrakis[methylene(3,5-di-tert-butyl-4-hydroxyhydro-cinnamate)]methane; bis[(beta-(3,5-ditert-butyl-4-hydroxybenzyl)-methylcarboxyethyl)]sulphide, 4,4'-thiobis(2-methyl-6-tert-butylphenol), 4,4'-thiobis(2-tert-butyl-5-methylphenol), 2,2'-thiobis(4-methyl-6-tert-butylphenol), and thiodiethylene bis(3,5-di-tert-butyl-4-hydroxy)hydrocinnamate; phosphites and phosphonites such as tris(2,4-di-tert-butylphenyl)phosphite and di-tertbutylphenyl-phosphonite; thio compounds such as dilaurylthiodipropionate, dimyristylthiodipropionate, and distearylthiodipropionate; various siloxanes; polymerized 2,2,4-trimethyl-1,2-dihydroquinoline, n,n'-bis(1,4-dimethylpentyl-p-phenylenediamine), alkylated diphenylamines, 4,4'-bis(alpha,alpha-dimethylbenzyl)diphenylamine, diphenyl-p-phenylenediamine, mixed di-aryl-p-phenylenediamines, and other hindered amine anti-degradants or stabilizers. Nonlimiting examples of suitable antioxidants include Topanol® CA, Vanox® 1320, Irganox® 1010, Irganox® 245 and Irganox® 1076. The antioxidant or antioxidants may be added to the plasticizer composition of this disclosure. Antioxidants can be used in amounts of 0.01 to 5 wt % based on the weight of the polymeric composition.

In an embodiment, the polymeric composition includes a heat stabilizer. Nonlimiting examples of suitable heat stabilizers include lead-free mixed metal heat stabilizers, lead stabilizers, organic heat stabilizers, epoxides, salts of monocarboxylic acids, phenolic antioxidants, organic phosphites, hydrotalcites, zeolites, perchlorates and/or betadiketones. Nonlimiting examples of suitable betadiketones are dibenzoylmethane, palmitoyl benzoyl methane, stearoyl benzoyl methane and mixtures thereof. A nonlimiting example of suitable dibenzoylmethane is Rhodiastab® 83. A nonlimiting example of suitable mixtures of palmitoyl benzoyl methane and stearoyl benzoyl methane is Rhodiastab® 50. Nonlimiting examples of suitable lead-free mixed metal heat stabilizers include Mark® 6797, Mark® 6776 ACM, Mark® 6777ACM, Therm-Chek® RC215P, Therm-Chek® 7208, Naftosafe® EH-314, Baeropan® MC 90400 KA, Baeropan® MC 90400 KA/1, Baeropan® MC8553 KA-ST 3-US, Baeropan® MC 9238 KA-US, Baeropan® MC 90249 KA, and Baeropan® MC 9754 KA. The heat stabilizer or heat stabilizers may be added to the plasticizer composition of this disclosure. Heat stabilizers can be used in amounts of 0.1 to 10 wt % based on the weight of the polymeric composition.

In an embodiment, the polymeric composition includes a lubricant. Nonlimiting examples of suitable lubricants include stearic acid, metal salts of stearic acid, paraffin wax, and polyethylene glycols. The lubricants may be used alone or in combination. The lubricant may also be combined with the heat stabilizer.

In an embodiment, the polymeric composition includes a processing aid. Nonlimiting examples of suitable processing aids include metal salts of carboxylic acids such as zinc stearate or calcium stearate; fatty acids such as stearic acid, oleic acid, or erucic acid; fatty amides such as stearamide, oleamide, erucamide, or N,N'-ethylene bis-stearamide; polyethylene wax; oxidized polyethylene wax; polymers of ethylene oxide; copolymers of ethylene oxide and propylene oxide; vegetable waxes; petroleum waxes; non ionic surfactants; and polysiloxanes. Processing aids can be used in amounts of 0.05 to 5 wt % based on the weight of the polymeric composition.

The polymeric compositions are generally prepared according to conventional dry blend or wet blend methods known to those skilled in the art of PVC compounding. The mixtures obtained from the blending process can be further compounded with a mixer such as a Banbury batch mixer, a Farrel Continuous Mixer, or a single or twin screw extruder.

In an embodiment, the polymeric composition is made by absorption of the plasticizers of this disclosure in PVC powder to make a dry blend. Any suitable method/apparatus may be used to make the dry blend including, but not limited to, a Henschel mixer or a ribbon blender. The polymeric composition may contain other additives in addition to the PVC and the plasticizer. The dry blend may then be further compounded (via melt extrusion for example) and formed into any desired shape (film, pellet, etc.).

With an optimal stabilizer and antioxidant package, the polymeric compositions of this disclosure are suitable for applications requiring long term dry or wet insulation resistance testing at elevated temperatures, and other demanding applications where temperatures are as high as 136° C. (either in air or while immersed in oils).

The present polymeric composition(s) may comprise two or more embodiments disclosed herein.

The surprising properties of flexibility, low plasticizer volatility, low migration, low viscosity and/or high solution temperature exhibited by the present polymeric composition make it well suited for wire and cable coating applications, and high temperature wire/cable applications in particular. Accordingly, the present disclosure provides a coated conductor. A "conductor" is an element of elongated shape (wire, cable, fiber) for transferring energy at any voltage (DC, AC, or transient). The conductor is typically at least one metal wire or at least one metal cable (such as aluminum or copper) but may include optical fiber.

In an embodiment, a coated conductor is provided and includes a conductor and a coating on the conductor. The coating is composed of the present composition which includes the polymeric resin and the present plasticizer composition containing one, two, three, or more plasticizers. The polymeric resin of the coating may be any polymeric resin disclosed herein. The plasticizer composition may be any plasticizer composition composed of one or more AFE alone or blended with one or more EPA and/or blended with one or more other plasticizers as disclosed herein.

A "metal conductor," as used herein, is at least one metal wire and/or at least one metal cable. The coated metal conductor may be flexible, semi-rigid, or rigid. The coating (also referred to as a "jacket" or a "sheath" or "insulation") is on the metal conductor or on another polymeric layer around the conductor. The coating includes the present composition. The composition may be any composition as disclosed herein. As used herein, "on" includes direct contact or indirect contact between the coating and the metal conductor. "Direct contact" is a configuration whereby the coating immediately contacts the metal conductor, with no intervening layer(s) and/or no intervening material(s) located between the coating and the metal conductor. "Indirect contact" is a configuration whereby an intervening layer(s) and/or an intervening structure(s) and/or intervening material(s) is/are located between the metal conductor and the coating. The coating may wholly or partially cover or otherwise surround or encase the metal conductor. The coating may be the sole component surrounding the metal conductor. Alternatively, the coating may be one layer of a multilayer jacket or sheath encasing the metal conductor.

In an embodiment, the polymeric resin is a vinyl chloride resin such as PVC as discussed above. The PVC is blended with the plasticizer composition to form the coating. The coating may include additional components. In an embodiment, the coating includes from about 1 wt % to about 99 wt % or from about 20 wt % to about 80 wt %, or from about 30 wt % to about 70 wt % PVC and from 99 wt % to about 1 wt %, or from about 80 wt % to about 20 wt %, or from about 70 wt % to about 30 wt % plasticizer composition. In a further embodiment, the coating contains from about 30 wt % to about 90 wt % PVC and from about 70 wt % to about 10 wt % of the plasticizer composition.

The plasticizer composition may be any plasticizer composition disclosed herein. In an embodiment, the plasticizer composition includes APE. The APE present in the coating has a hydroxyl number from 0 to less than 450, or from 0 to less than 200, or from 0 to less than 100, or from 0 to less than 50, or from 0 to less than 15, or from 0 to less than 10, or from 0 to less than 5, or from 0 to less than 2, or 0. The plasticizer composition may include a second plasticizer in addition to the APE.

The coating may have any of the properties as discussed above for the present composition. In an embodiment, the coated conductor passes the heat test as measured in accordance with UL-1581. In another embodiment, the plasticizer composition in the coating has a solution temperature from about 140° C. to about 200° C. In another embodiment, the coating has a Shore hardness from about A60 to about A100 as measured in accordance with ASTM D2240. In another embodiment, the coating has a Shore hardness from about D10 to about D70 as measured in accordance with ASTM D 2240. In an embodiment, the coating includes from about 30 wt % to about 90 wt % of polyvinyl chloride and from about 70 wt % to about 10 wt % of APE or APE/EFA plasticizer mixture.

Nonlimiting examples of suitable coated metal conductors include flexible wiring such as flexible wiring for consumer electronics, a power cable, a power charger wire for cell phones and/or computers, computer data cords, power cords, appliance wiring material, building wire, automotive wire, and consumer electronic accessory cords.

The present coated conductor may comprise two or more embodiments disclosed herein.

The coated conductor, such as a coated wire or a coated cable (with an optional insulation layer), with a jacket comprising the composition disclosed herein can be prepared with various types of extruders, e.g., single or twin screw types. A description of a conventional extruder can be found in U.S. Pat. No. 4,857,600. An example of co-extrusion and an extruder can be found in U.S. Pat. No. 5,575,965. A typical extruder has a hopper at its upstream end and a die at its downstream end. The hopper feeds into a barrel, which contains a screw. At the downstream end, between the end of the screw and the die, there is a screen pack and a breaker plate. The screw portion of the extruder is considered to be divided up into three sections, the feed section, the compression section, and the metering section, and two zones, the back heat zone and the front heat zone, the sections and zones running from upstream to downstream. In the alternative, there can be multiple heating zones (more than two) along the axis running from upstream to downstream. If it has more than one barrel, the barrels are connected in series. The length to diameter ratio of each barrel is in the range of about 15:1 to about 30:1.

The wire and cable constructions (i.e., a coated metal conductor) of this disclosure are made by extruding the present composition onto the conductor or onto the bundle of insulated conductors to form a coating (or a jacket) around the insulated conductors. The thickness of the jacket or insulation depends on the requirements of the desired end use application. Typical thickness of the jacket or insulation is from about 0.010 inches to about 0.200 inches, or from about 0.015 inches to about 0.050 inches. The present composition may be extruded into the jacket from previously made composition. Usually the present composition is in the form of pellets for easy feeding into the extruder. The wire and cable jacket or insulation may be extruded directly from the compounding extruder without going through the separate step of pelletizing the present composition. This one-step compounding/extrusion process would eliminate one heat history step for the composition.

A nylon layer may also be extruded over the insulation, such as in conventional THHN, THWN and THWN-2 constructions.

Nonlimiting examples of embodiments of the present disclosure are provided below.

In an embodiment E1, an acetylated polyglyceride fatty acid ester is provided and comprises: a polyglyceride with at least one fatty acid component having from about 4 to about 22 carbon atoms; and at least one acetyl group. E2. The acetylated polyglyceride fatty acid ester of E1 having a hydroxyl number from 0 to less than 450. E3. The acetylated polyglyceride fatty acid ester of E1-E2 having a viscosity from about 100 to about 3000 mPa at 25° C. as measured in accordance with ASTM D445. E4. The acetylated polyglyceride fatty acid ester of any of E1-E3 having a molecular weight from about 500 to about 2000 g/mol. E5. The acetylated polyglyceride fatty acid ester of any of E1-E4 wherein the polyglyceride moiety comprises tetraglycerol. E6. The acetylated polyglyceride fatty acid ester of any of E1-E5 wherein the fatty acid component is selected from the group consisting of lauric acid, 12-hydroxystearic acid, and combinations thereof.

In an embodiment E7, a composition is provided and comprises: an acetylated polyglyceride fatty acid ester; and an epoxidized fatty acid ester. E8. The composition of E7 comprising an acetylated polyglyceride fatty acid ester of any of E1-E6. E9. The composition of any of E7-E8 wherein the epoxidized fatty acid ester is selected from the group consisting of epoxidized soybean oil, epoxidized propylene glycol dioleate, epoxidized palm oil, epoxidized linseed oil, epoxidized fatty acid methyl esters, epoxidized derivatives of each of the foregoing, and combinations thereof. E10. The composition of any of E7-E9 comprising an acetylated polyglyceride fatty acid ester having a hydroxyl number from 0 to less than 450; and epoxidized soybean oil. E11. The composition of any of E7-E10 comprising a second epoxidized fatty acid ester.

In an embodiment E12, a polymeric composition is provided and comprises: a polymeric resin; and a plasticizer composition comprising an acetylated polyglyceride fatty acid ester and optionally an epoxidized fatty acid ester. E13. The polymeric composition of E12 comprising a plasticizer composition of any of claims E1-E11. E14. The polymeric composition of any of E11-E13 wherein the polymeric resin comprises a vinyl chloride resin. E15. The polymeric composition of any of E12-E14 wherein the plasticizer composition comprises a first epoxidized fatty acid ester and a second epoxidized fatty acid ester. E16. The polymeric composition of any of E12-E15 wherein the polymeric composition is a plaque having a tensile elongation after 168 hours heat aging 136° C. of greater than 30%. E17. The polymeric composition of any of E12-E16 having a volume resistivity from about 1.0E+10 to about 1.0E+17 Ohm cm.

In an embodiment E18, a coated conductor is provided and comprises: a conductor; and a coating on the conductor, the coating comprising a polymeric resin and a plasticizer composition comprising an acetylated polyglyceride fatty acid ester and optionally an epoxidized fatty acid ester. E19. The coated conductor of E18 wherein the coating comprises a composition of any of E1-E17. E20. The coated conductor of any of E18-E19 wherein coated conductor passes the heat test as determined in accordance with UL-1581.

Test Methods

Acid number (or "acid value") is a measure of the amount of free acid present in a compound. The acid number is the number of milligrams of potassium hydroxide required for the neutralization of free acid (fatty acid and/or other acid such as acetic acid, for example) present in one gram of a substance. The acid number is determined in accordance with German Standard DIN 53402 (mg KOH/g).

APHA color is measured using Color Quest XE colorimeter, available from HunterLab, or equivalent; 20-mm transmission cell; HunterLab Universal software, version 4.10 or equivalent; Black and White color reference titles available from HunterLab, or equivalent; the measured APHA color value of deionized (DI) water is zero.

Density at 25° C. is determined in accordance with German Standard DIN 51 757 (g/cm$^3$).

Glass transition temperature (Tg) is determined by dynamic mechanical analysis (DMA) using a TA Instrument AR1000N Rheometer having DMA fixtures. The specimen is in the form of a rectangular solid and tested in tension mode. The temperature is varied from −100° C. to +160° C. at a ramp rate of 5° C./min, and the test frequency is held constant at 6.283 rad/s (1 Hz). The storage and loss modulus of the sample, as well as the tan delta, are measured as a function of the temperature. The glass transition temperature (Tg) is determined from the peak tan delta measurement.

Hydroxyl Number (or hydroxyl value) is an indication of the degree of acetylation and is a measure of the number of hydroxyl groups present in a polymer. The hydroxyl number is the number of milligrams of potassium hydroxide required to neutralize the hydroxyl groups in one gram of polymer. The hydroxyl number is determined in accordance with German Standard DIN 53 240 (mg KOH/g).

Iodine Number is an indication of the degree of hydrogenation and is determined in accordance with German Einheitsmethode DGF C-V 11a (53) (g I$_2$/100 g).

Plasticizer compatibility in the polymeric composition is assessed by visual inspection of molded or extruded specimens aged at elevated temperatures (e.g., 113° C. or 136° C.) for defined lengths of time (e.g., 7 days). The extruded specimens may be in the form of a wire (i.e., insulation extruded over conductor). The amount of exudate (spew) on surface after 7 days at 113° C. or 136° C. is rated as "none", "slight", "moderate", or "heavy".

Shore hardness is determined in accordance with ASTM D 2240.

Solution Temperature is the temperature at which a heterogeneous mixture of plasticizer and a PVC resin is observed to change to a single phase. Solution temperature is determined by immersing 1 gram PVC in 20 grams of plasticizer and increasing the temperature stepwise until the PVC is seen to be completely dissolved by observation under a microscope, in accordance with German Standard DIN 53 408 (° C.).

Surface smoothness of coated conductors (extruded wires) is measured using a surface roughness measuring apparatus made by Mitutoyo of Japan, in accordance with ANSI/ASME B46.1.

Temperature of 5% mass loss (° C.) is determined using TG/DTA. 220. The plasticizer specimen is heated from room temperature up to 600° C. at 10 K/min under inert gas purge, and the appearing mass loss and thermal effects are recorded in thermograms. The higher the temperature for 5% mass loss, the lower the volatility.

Tensile strength (TS), tensile strength retention (TSR), tensile elongation (TE), and tensile elongation retention (TER) (at 2 inch/min) on unaged specimens, on specimens aged at 113° C. or at 136° C. for 168 hours, and on specimens aged in IRM902 oil at 100° C. for 96 hours is determined in accordance with ASTM D638 and UL 1581/2556 either on dogbones cut from molded plaques or tubular insulations removed from coated conductors (extruded wires).

The term "UL 1581" is Underwriters Laboratories Reference Standard for Electrical Wires, Cables, and Flexible Cords. UL 1581 contains specific details for conductors, insulation, jackets and other coverings, and for methods of sample preparation, specimen selection and conditioning, and for measurement and calculation that are required in wire and cable standards.

Viscosity is determined in accordance with Standard ASTM D445, Brookfield-Viscosimeter at 25° C. and/or 40° C.

Volume resistivity (Vol Res) (Ohm-cm) at 23° C., is measured with 500 volts direct current, in accordance with ASTM D257. Specimens of 3.5 inch diameter are cut from 40 mil thick molded plaques and tested using a Hewlett Packard 16008A Resistivity Cell connected to a Hewlett Packard 4329A High Resistance Meter.

Water content is determined in accordance with German Standard DIN 51 777(%).

Weight Retained (Wt. Ret.) (%) after 7 Days at 136° C. is measured on specimens of 1.25 inch diameter that are cut from 30 mil thick molded plaques.

By way of example, and not by limitation, examples of the present disclosure are provided.

EXAMPLES

A. Acetylated Polyglyceride Fatty Acid Esters

Examples 1-6

Example 1

Preparation of nominal acetylated monoester of tetraglycerol and lauric acid. The tetraglycerol is synthesized by condensation of glycerol and its properties are as follows: hydroxyl number of 1060 mg KOH/g and molecular weight of 314.4 g/mol. It also contains 9.1 wt % glycerol, as well as different amounts of diglycerol, triglycerol, tetraglycerol, pentaglycerol and hexaglycerol with following distribution in area %, determined by gas chromotagraphy (GC) after derivatization and set forth in Table A below.

TABLE A

| Component | Area % Tetraglycerol Used for Examples 1 to 5 | Area % Tetraglycerol Used for Example 6 | Area % Sakamoto R-PG Polyglycerol-3 Used for Examples 6A, 6B, 6C, and 6D |
|---|---|---|---|
| Glycerol | 14.8 | 13.5 | <0.1 |
| Cycl. Dimers | 6.0 | 6.6 | 0.2 |
| Diglycerol | 27.7 | 25.3 | 33.2 |
| Cycl. Trimers | 2.4 | 2.9 | 0.9 |
| Triglycerol | 19.7 | 19.8 | 47.5 |
| Not identified | 2.4 | 2.7 | 1.4 |
| Tetraglycerol | 10.8 | 11.4 | 12.2 |
| Pentaglycerol | 7.4 | 9.0 | 2.8 |
| Hexaglycerol | 8.5 | 7.7 | 1.4 |

62.9 g (0.20 mol) tetraglycerol (as received from oligomerization of glycerol), 40.1 g (0.20 mol) lauric acid and 0.26 g catalyst Tin(II)octoate are added to a 1 L one-neck glass flask. The flask is fixed to a rotation evaporator. After heating to 160° C., the flask is flushed with nitrogen and evacuated (3-5 times). The pressure is adjusted to approximately 10-20 mbar and the reaction is monitored via distillation of water. The reaction is stopped after 4 hours by cooling to room temperature.

112.3 g (1.1 mol) acetic anhydride is added and the flask is heated to 100° C. (under normal pressure). After 3 hours, the temperature is increased to 120° C. for 1 hour. The temperature is increased again stepwise (30 min, 10° C., normal pressure) to 150° C. and residual acetic acid and acetic anhydride is distilled off.

The product, acetylated polyglyceride lauric acid monoester (average degree of polymerization=4), is a light yellow liquid. Yield: 99% (calculated on tetraglycerol).

Example 2

Preparation of nominal acetylated ester mixture of tetraglycerol and lauric acid. The tetraglycerol is the same as used in Example 1.

62.9 g (0.20 mol) tetraglycerol (as received from oligomerization of glycerol), 20.05 g (0.10 mol) lauric acid and 0.21 g catalyst Tin(II)octoate are added to a 1 L one-neck glass flask. The flask is fixed to a rotation evaporator. After heating to 160° C., the flask is flushed with nitrogen and evacuated (3-5 times). The pressure is adjusted to approximately 10-20 mbar and the reaction is monitored via distillation of water. The reaction is stopped after 4 hours by cooling to room temperature.

123.5 g (1.21 mol) acetic anhydride is added and the flask is heated to 100° C. (under normal pressure). After 3 hours, the temperature is increased to 120° C. for 1 hour. The temperature is increased again stepwise (30 min, 10° C., normal pressure) to 150° C. and residual acetic acid and acetic anhydride is distilled off.

The product, acetylated polyglyceride lauric acid ester (mixture) (average degree of polymerization=4), is a light yellow liquid. Yield: 99% (calculated on tetraglycerol).

Example 3

Preparation of nominal acetylated monoester of tetraglycerol and palm kernel oil fatty acid. The tetraglycerol is the same as used in Example 1.

94 g (0.3 mol) tetraglycerol (as received from oligomerization of glycerol) and 70 g (0.1 mol) palm kernel oil are introduced in an autoclave cylinder. The cylinder is closed and put into the heating mantle. The mixture is heated with mechanical stirring (400 rpm) at a temperature of 240° C. for 13 hours. The product is a yellow liquid product (monoester of tetraglycerol and palm kernel oil fatty acid).

90 g of monoester of tetraglycerol and palm kernel oil fatty acid and 108 g acetic anhydride are added to a 250 mL flask. The reaction is performed under a vacuum rotation evaporator at 120° C. for 3 hours. A vacuum of 700-50 mbar is used to remove residual acetic acid/anhydride. The product is acetylated polyglyceride palm kernel oil fatty acid monoester.

Example 4

Preparation of nominal acetylated triester of tetraglycerol and palm kernel oil fatty acid. The tetraglycerol is the same as used in Example 1.

47 g (0.15 mol) tetraglycerol (as received from oligomerization of glycerol) and 105 g (0.15 mol) palm kernel oil are introduced in an autoclave cylinder. The cylinder is closed and put into the heating mantle. The mixture is heated with mechanical stirring (400 rpm) at a temperature of 240° C. for 13 hours. The product is a yellow liquid product (triester of tetraglycerol and palm kernel oil fatty acid).

110 g of triester of tetraglycerol and palm kernel oil fatty acid and 75 g acetic anhydride are added to a 250 mL flask. The reaction is performed under a vacuum rotation evaporator at 120° C. for 3 hours. A vacuum of 700-50 mbar is used to remove residual acetic acid/anhydride. The product is acetylated polyglyceride palm kernel oil fatty acid triester.

Example 5

Preparation of nominal acetylated monoester of tetraglycerol and 12-hydroxystearic acid. The tetraglycerol is the same as used in Example 1.

56.6 g (0.18 mol) tetraglycerol (as received from oligomerization of glycerol), 54.1 g (0.18 mol) 12-hydroxystearic acid and 0.28 g catalyst Tin(II)octoate are added to a 1 L one-neck glass flask. The flask is fixed to a rotation evaporator. After heating to 160° C., the flask is flushed with nitrogen and evacuated (3-5 times). The pressure is adjusted to approximately 10-20 mbar and the reaction is monitored via distillation of water. The reaction is stopped after 4 hours by cooling to room temperature.

121.3 g (1.19 mol) acetic anhydride is added and the flask is heated to 100° C. (under normal pressure). After 3 hours, the temperature is increased to 120° C. for 1 hour. The temperature is increased again stepwise (30 min, 10° C., normal pressure) to 150° C. and residual acetic acid and acetic anhydride is distilled off.

The product, acetylated polyglyceride and 12-hydroxystearic acid monoester (average degree of polymerization=4), is a light yellow liquid. Yield: 99% (calculated on tetraglycerol).

Example 6

Preparation of nominal acetylated monoester of tetraglycerol and lauric acid. The tetraglycerol is synthesized by condensation of glycerol and its properties are as follows: hydroxyl number of 1084 mg KOH/g and molecular weight of 314.4 g/mol. It also contains 7.6 wt % glycerol, as well as different amounts of diglycerol, triglycerol, tetraglycerol, pentaglycerol and hexaglycerol with distribution in area %, determined by gas chromatography (GC) after derivatization, as set forth in Table A.

1932 g tetraglycerin (as received from oligomerization of glycerol) and 1231 g lauric acid are charged in a 5 L reactor. The reactor with mechanical stirrer and common distillation glassware is heated by an external bath to a temperature of 100° C. The reactor is flushed with nitrogen and evacuated three times. After adding 8 g Tin (II) octoate as catalyst, the reactor is heated to 180° C. Water formed is distilled off using vacuum of 200 mbar. The reaction is stopped after 6 hours at an acid number of 1.1 mg KOH/g.

The intermediate ester is acetylated in two portions. 1488 g intermediate ester is taken out of the reactor and 1770 g acetic anhydride is added to the remaining 1564 g ester. The reactor is heated to 120° C. and this temperature maintained over 4 hours. Vacuum from 400 to 100 mbar is used to remove acetic acid and residual acetic anhydride at a bath temperature of 120° C. The product (dark yellow, slightly cloudy, acid number of 3.1 mg KOH/g) is taken out of the reactor. After that the other portion intermediate ester (1488 g) and 1700 g acetic anhydride are charged into the reactor and the reaction performed analogously. The two portions are mixed in the reactor by stirring at 50° C. A yellow liquid is obtained (4165 g).

Example 6A

Preparation of nominal acetylated monoester of polyglycerol and lauric acid. The polyglycerol is R-PG Polyglycerol-3 (product of Sakamoto Yakuhin Kogyo) and its properties are as follows: hydroxyl number of 1173 mg KOH/g and molecular weight of 240.3 g/mol. It also contains less than 0.1 wt % glycerol, as well as different amounts of diglycerol, triglycerol, tetraglycerol, pentaglycerol and hexaglycerol with distribution in area %, determined by gas chromatography (GC) after derivatization, as set forth in Table A.

120 g polyglycerin (R-PG Polyglycerol-3), 100.15 g lauric acid and 0.55 g Tin (II) octoate (catalyst) are charged in a 1 L flask. The reaction is carried out using a vacuum rotation evaporator. After heating to 160° C., the flask is flushed with nitrogen and evacuated three times. The reaction is followed by measurement of the distilled water and determination of the acid number. The reaction is stopped at an acid number of 3 mg KOH/g after 12 hours at 180° C. and 300-12 mbar. The product is a cloudy paste, with the following properties: Acid Number: 3.3 mg KOH/g; Saponification Number: 130 mg KOH/g; Hydroxyl Number: 577 mg KOH/g.

138.6 g acetic anhydride is added to 120 g of the product, the mixture heated to 115° C. and the temperature maintained at 115° C. over 4 hours. Vacuum is used to remove acetic acid and residual acetic anhydride at a bath temperature of 115° C. A liquid product is obtained.

Example 6B

Preparation of nominal acetylated diester of polyglycerol and lauric acid. The polyglycerol is R-PG Polyglycerol-3 (product of Sakamoto Yakuhin Kogyo) and its properties are as follows: hydroxyl number of 1173 mg KOH/g and molecular weight of 240.3 g/mol. It also contains less than 0.1 wt % glycerol, as well as different amounts of diglycerol, triglycerol, tetraglycerol, pentaglycerol and hexaglycerol with distribution in area %, determined by gas chromatography (GC) after derivatization, as set forth in Table A.

80 g polyglycerin (R-PG Polyglycerol-3), 133.5 g lauric acid and 0.53 g Tin (II) octoate (catalyst) are charged in a 1 L flask. The reaction is carried out using a vacuum rotation evaporator. After heating to 160° C., the flask is flushed with nitrogen and evacuated three times. The reaction is followed by measurement of the distilled water and determination of the acid number. The reaction is stopped at an acid number of 2.0 mg KOH/g after 11 hours at 180° C. and 300-12 mbar. The product is a cloudy paste, with the following properties: Acid Number: 2.0 mg KOH/g; Hydroxyl Number: 280.8 mg KOH/g.

70.5 g acetic anhydride is added to 120 g of the product, the mixture heated to 120° C. and the temperature maintained at 120° C. over 4 hours. Vacuum is used to remove acetic acid and residual acetic anhydride at a bath temperature of 120° C. A liquid product was obtained.

Example 6C

Preparation of nominal acetylated monoester of polyglycerol and 12-Hydroxystearic acid. The polyglycerol is R-PG Polyglycerol-3 (product of Sakamoto Yakuhin Kogyo) and its properties are as follows: hydroxyl number of 1173 mg KOH/g and molecular weight of 240.3 g/mol. It also contains less than 0.1 wt % glycerol, as well as different amounts of diglycerol, triglycerol, tetraglycerol, pentaglycerol and hexaglycerol with distribution in area %, determined by gas chromatography (GC) after derivatization, as set forth in Table A.

80 g polyglycerin (R-PG Polyglycerol-3), 100.17 g 12-Hydroxystearic acid and 0.45 g Tin (II) octoate (catalyst) are charged in a 1 L flask. The reaction is carried out using a vacuum rotation evaporator. After heating to 160° C., the flask is flushed with nitrogen and evacuated three times. The reaction is followed by measurement of the distilled water and determination of the acid number. The reaction is stopped at an acid number of 1.3 mg KOH/g after 11 hours at 180° C. and 300-12 mbar. The product is yellow and has two phases. The lower phase is separated (35.42 g=19.7%) and the upper phase (132 g) is characterized. The upper phase is solid with the following properties: Acid Number: 1.3 mg KOH/g; Saponification Number: 130 mg KOH/g; Hydroxyl Number: 348.8 mg KOH/g.

80 g acetic anhydride is added to 111 g of the upper phase, the mixture heated to 115° C. and the temperature maintained at 115° C. over 4 hours. Vacuum is used to remove acetic acid and residual acetic anhydride at a bath temperature of 115° C. A liquid product is obtained.

Example 6D

Preparation of nominal acetylated diester of polyglycerol and 12-Hydroxystearic acid. The polyglycerol is R-PG Polyglycerol-3 (product of Sakamoto Yakuhin Kogyo) and its properties are as follows: hydroxyl number of 1173 mg KOH/g and molecular weight of 240.3 g/mol. It also contains less than 0.1 wt % glycerol, as well as different amounts of diglycerol, triglycerol, tetraglycerol, pentaglycerol and hexaglycerol with distribution in area %, determined by gas chromatography (GC) after derivatization, as set forth in Table A.

51.5 g polyglycerin (R-PG Polyglycerol-3), 128.9 g 12-Hydroxystearic acid and 0.45 g Tin (II) octoate (catalyst) are charged in a 1 L flask. The reaction is carried out using a vacuum rotation evaporator. After heating to 160° C., the flask is flushed with nitrogen and evacuated three times. The reaction is followed by measurement of the distilled water and determination of the acid number. The reaction is stopped at an acid number of 0.7 mg KOH/g after 7 hours at 180° C. and 300-12 mbar. The product is solid with the following properties: Acid Number: 0.7 mg KOH/g; Hydroxyl Number: 331 mg KOH/g.

83 g acetic anhydride is added to 120 g of the product, the mixture heated to 120° C. and the temperature maintained at 120° C. over 4 hours. Vacuum is used to remove acetic acid and residual acetic anhydride at a bath temperature of 120° C. A liquid product is obtained.

Table 1 below sets forth the properties for Examples 1-6, 6A, 6B, 6C and 6D.

TABLE 1

| Ex. | Name | AN | OHN | Density, 25° C. g/cm³ | Solution Temp. ° C. | Temp. of 5% mass loss ° C. | Water Content (%) | Viscosity (mPas) at 25° C. |
|---|---|---|---|---|---|---|---|---|
| 1 | Acetylated polyglyceride lauric acid monoester | 6.5 | 0 | 1.09 | 169 | 211 | 0.02 | 247 |
| 2 | Acetylated polyglyceride lauric acid ester (mixture) | 6.3 | 0 | 1.13 | 180 | 207 | 0.02 | |
| 3 | Acetylated polyglyceride palm kernel oil fatty acid ester | 7.1 | 0 | 1.09 | 168 | 196 | n/a | |
| 4 | Acetylated polyglyceride palm kernel oil fatty acid triester | 2.5 | 0 | 1.02 | 177 | 218 | n/a | |
| 5 | Acetylated polyglyceride 12-hydroxystearic acid monoester | 1.7 | 0 | 1.08 | 165 | 244 | 0.02 | |
| 6 | Acetylated polyglyceride lauric acid monoester | 3.0 | 0 | 1.09 | 170 | 212 | 0.03 | 310 |
| 6A | Acetylated polyglyceride lauric acid monoester | 2.4 | 0 | 1.07 | 165 | 255 | 0.01 | 225 |
| 6B | Acetylated polyglyceride lauric acid diester | 1.7 | 0 | 1.02 | 175 | 284 | 0.00 | 160 |
| 6C | Acetylated polyglyceride 12-hydroxystearic acid monoester | 1.1 | 9.2 | 1.01 | 173 | 275 | 0.01 | 635 |
| 6D | Acetylated polyglyceride 12-hydroxystearic acid diester | 1.8 | 0 | 1.01 | 178 | 292 | 0.01 | 680 |

AN = acid number DIN 53402 (mg KOH/g)
Density = DIN 51757
OHN = hydroxyl number, DIN 53240 (mg KOH/g)
Solution temp = DIN 53408
Temp. of 5% mass loss = TG/DTA 220
Viscosity = ASTM D445 Brookfield 25° C.
Water Content = DIN 51777

B. Thermoplastic Compositions: Blends of PVC, APE & EFA

Blends of polyvinylchloride (PVC) with various plasticizers and additives are prepared. The plasticizers evaluated are the APEs of Examples 1-6 and the plasticizers set forth in Table 2 below.

TABLE 2

| Abbreviation | Name | Source |
|---|---|---|
| ESO | Epoxidized soybean oil | PLAS-CHEK ® 775, Ferro |
| eFAME | epoxidized fatty acid methyl ester | Vikoflex ® 7010, Arkema |
| DOP | dioctyl phthalate | TCI America |
| DIDP | diisodecyl phthalate | TCI Japan |
| TINTM | triisononyl trimellitate | Sigma-Aldrich, America |
| TOTM | trioctyl trimellitate | Sigma-Aldrich, America |

PVC, plasticizer and additives are combined to prepare thermoplastic compositions. The components present in each thermoplastic composition are provided in Table 3 below. The preparation procedure for each thermoplastic composition follows Table 3.

TABLE 3

Composition of Examples 7-21 and Comparative Samples (CS) 1-12

| | Examples 7-10 and CS 1-3 | Examples 11-15 and CS 4-7 | CS 8 | Example 16 CS 9-10 | Example 17 | Example 18 | Example 19 CS 11 | Example 20 CS 12 | Example 21 |
|---|---|---|---|---|---|---|---|---|---|
| PVC | 63.9 | 63.9 | 63.9 | 63.9 | 63.9 | 63.9 | 63.9 | 60.3 | 62.3 |
| Plasticizer | 23.8 (87)* | 23.8 (87)* | n/a (ESO is sole plasticizer) | 27.3 DIDP, TOTM or Ex 1 (87)* ESO (13)* | 27.3 Ex 1 (65)* ESO (35)* | 27.3 Ex 1 (43)* ESO (57)* | 23.8 (87)* | 30.0 (100)* Ex 6 or TOTM | 30.0 Ex. 6 (50)* ESO (50)* |
| CaCO₃ | 6.4 | 6.4 | — | 6.4 | 6.4 | 6.4 | — | — | — |
| Polyfil ® 70 Clay | n/a | n/a | 6.4 | n/a | n/a | n/a | 6.4 | — | — |
| Satintone ® SP-33 Clay | — | — | — | — | — | — | — | 6.4 | 6.4 |
| ESO | 3.5 (13)* | 3.5 (13)* | 27.3 (100)* | — | — | — | 3.5 (13)* | — | — |
| DBDL | 2.1 | — | — | — | — | — | — | — | — |
| Mark ® 6797 | — | 2.1 | 2.1 | 2.1 | 2.1 | 2.1 | 2.1 | — | — |

TABLE 3-continued

Composition of Examples 7-21 and Comparative Samples (CS) 1-12

|  | Examples 7-10 and CS 1-3 | Examples 11-15 and CS 4-7 | CS 8 | Example 16 CS 9-10 | Example 17 | Example 18 | Example 19 CS 11 | Example 20 CS 12 | Example 21 |
|---|---|---|---|---|---|---|---|---|---|
| Baeropan ® MC 90249 KA | — | — | — | — | — | — | — | 3.0 | 1.0 |
| Irganox ® 1076 | 0.3 | 0.3 | 0.3 | 0.3 | 0.3 | 0.3 | 0.3 | 0.3 | 0.3 |

Baeropan ® MC 90249 KA = calcium-zinc heat stabilizer (Baerlocher)
$CaCO_3$ = Hubercarb ® Q1T calcium carbonate
Polyfil ® 70 = kaolin clay
DBDL = dibutyltin dilaurate (T-12 Dabco)
Irganox ® 1076 = hindered phenolic antioxidant (Ciba Chemicals)
Mark ® 6797 = calcium-zinc stabilizer (Chemtura Corp.)
PVC = polyvinyl chloride homopolymer (OxyVinyls ® 240F)
Satintone ® SP-33 = calcined clay
Values = wt % based on total weight of composition
*Wt % based on weight of total plasticizer The following procedure is used to prepare the thermoplastic compositions for Examples 7-15 and Comparative Samples (CS) 1-8
 Weigh the individual ingredients and mix all in a container using a spatula
 Use "40 $cm^3$" Brabender mixing bowl with conventional rotors to make batches of each formulation at 40 rpm setting
 Do not purge mixing bowl with nitrogen
 Add mixture of PVC and other ingredients, and mix at 175° C. for 5 minutes The blend compositions from the mixing bowl are compression molded into 30 mil thick plaques at 175° C. for 5 minutes for testing of all properties except volume resistivity. Volume resistivity is measured on specimens cut from 40 mil thick molded plaques.

The following procedure is used to prepare the thermoplastic compositions of Examples 16-18 and Comparative Samples (CS) 9-10.

Blends of polyvinylchloride (PVC) and three different plasticizer mixtures (and additives) are prepared in Examples 16 to 18 and comparative samples 9 to 10. Each plasticizer mixture is composed of acetylated monoester of tetraglycerol and lauric acid (APE) (from Example 1 above) or DIDP or TOTM and PLAS-CHEK® 775 epoxidized soybean oil (ESO). Three different plasticizer mixtures (Examples 16-18) are prepared with the following APE-to-ESO weight ratio and two different comparative samples are prepared with the following DIDP-to-ESO weight ratio or TOTM-to-ESO weight ratio (based on total weight of the plasticizer mixture) as shown in Table B:

TABLE B

| wt % | DIDP | TOTM | APE | ESO |
|---|---|---|---|---|
|  |  |  | 87 | 13 |
|  |  |  | 65 | 35 |
|  |  |  | 43 | 57 |
|  | 87 |  |  | 13 |
|  |  | 87 |  | 13 |

Wt % based on total wt plasticizer mixture

Weigh the individual ingredients and mix all in a container using a spatula
 Use a "40 $cm^3$" Brabender mixing bowl with conventional rotors to make batches of each formulation at 40 rpm setting
 Do not purge mixing bowl with nitrogen
 Add PVC and other ingredients, and mix at 175° C. for 5 minutes The blend compositions are removed from the mixing bowl and are compression molded at 175° C. for 5 minutes for testing of all properties except volume resistivity. Volume resistivity is measured on specimens cut from 40 mil thick molded plaques.

The following procedure is used to prepare Example 19 and Comparative Sample (CS) 11.
 Preheat APE of Example 6, TOTM and epoxidized soybean oil to 60° C. for minimum 30 minutes, shake and make the plasticizer mixtures (87/13 wt % APE/ESO or 87/13 wt % TOTM/ESO)
 Weigh the individual solid ingredients and mix all in a container using a spatula
 Use a Henschel mixer to mix 1 kg of 'dry blend' at a set temperature of 80° C. and 1800 rpm, by first fluxing the solids mixture and then adding the plasticizer, recording time for plasticizer sorption to be completed.
 The 'dry blend' is melt mixed using a conical twin screw extruder (25:1 L/D) at 45 rpm and the following set temperature profiles:
  CS11: zone 1=160° C., zone 2=165° C., zone 3=170° C., die=175° C.
  Ex 19: zone 1=155° C., zone 2=165° C., zone 3=175° C., die=180° C.
 The extruded strands are subsequently air cooled and pelletized.

The pellets are compression molded at 175° C. for 5 minutes. Specimens are cut from 30 mil molded plaques for testing of all properties except volume resistivity. Volume resistivity is measured on specimens cut from 40 mil thick molded plaques. The pellets are also used to fabricate wire/cable by coating onto a 0.064 inch (14 AWG) solid copper conductor using 25:1 single-screw extruder at set temperatures of 160° C., 165° C.; 170° C.; and 175° C. The outside diameter of the coated conductor is approximately 0.094 inch (approximately 0.015 inch thick wall). Die pressures during wire extrusion are noted.

The following procedure is used to prepare the thermoplastic compositions of Examples 20-29 and Comparative Sample (CS) 12.

Blends of polyvinylchloride (PVC), additives and different plasticizers (or a plasticizer mixture) are prepared in Examples 20 to 21 and comparative sample 12. The plasticizers are: (a) APE of Examples 6, 6A, 6B, 6C and 6D; (b)

Mixtures composed of 50 wt % APE of Examples 6, 6A, 6B, 6C and 6D and 50 wt % PLAS-CHEK® 775 ESO; and (c) TOTM. The following procedure is used to prepare the blends:

Preheat TOTM, APE, and epoxidized soybean oil to 60° C. for at least 60 minutes, shake and make a 50/50 wt % APE/ESO mixture (plasticizer composition)

Make "solids mixture" by mixing all ingredients (except plasticizer and clay) in a container using a spatula Make 'dry blends' by soaking plasticizer into PVC powder, as follows Use "40 cm$^3$" Brabender mixing bowl with sigma blades at 90° C. to make batches of each formulation at 40 rpm setting Do not purge mixing bowl with nitrogen After 2 min warm-up, add "solids mixture" and mix for 30 seconds Add plasticizer and mix for 6 minutes, and also observe how long it takes for plasticizer absorption to be completed (i.e., the physical appearance of the powder to change from "wet" to "dry")

Add filler (clay) and mix for 60 seconds

Stop and remove "dry blend"

The 'dry blend' is subsequently melt mixed using the following procedure:
(a) Mix in a "40 cm$^3$" Brabender mixing bowl with cam rotors at 40 rpm setting
(b) Do not purge mixing bowl with nitrogen
(c) Add 'dry blend', and mix at 180° C. for 2 minutes The blend composition is removed from the mixing bowl and is compression molded at 180° C. for 5 minutes. Specimens are cut from 30 mil thick molded plaques for testing of all properties except volume resistivity and Shore hardness. Volume resistivity is measured on specimens cut from 40 mil thick molded plaques. Shore hardness is measured on molded specimens of 250 mil thickness.

Properties for the thermoplastic compositions are provided in Tables 4-9 below.

TABLE 4

| Plasticizer Mixture† | Shore A Hardness ASTM D2240 | Tg (° C.) | TS (Unaged) - psi | TSR (%) after 113° C. Aging | TSR (%) after 136° C. Aging | TE (Unaged) - % | TER (%) after 113° C. Aging | TER (%) after 136° C. Aging | Vol Res |
|---|---|---|---|---|---|---|---|---|---|
| Example 7 Ex 1 (87) ESO (13) | 90.7 | 36.5 | 3558 | 109 | 142 | 243 | 80 | 39 | |
| Example 8 Ex 2 (87) ESO (13) | 88.9 | 35.3 | 3712 | 113 | 180 | 241 | 81 | 4 | |
| Example 9 Ex 3 (87) ESO (13) | 89.3 | 36.1 | 3432 | 143 | 177 | 240 | 79 | 3 | |
| Example 10 Ex 4 (87) ESO (13) | 91.1 | 50.8 | 3847 | 111 | 128 | 154 | 81 | 104 | |
| CS 1 DIDP (87) ESO (13) | 90.0 | 38.6 | 3177 | 106 | 203 | 234 | 69 | 4 | |
| CS 2 DOP (87) ESO (13) | 85.6 | 28.3 | 2993 | 191 | 217 | 254 | 11 | 4 | |
| CS 3 e-FAME (87) ESO (13) | 81.5 | 15.2 | 2607 | 218 | 242 | 249 | 8 | 6 | |
| Example 11 Ex 1 (87) ESO (13) | 90.7 ± 0.3 | 28.3 | 3083 ± 774 | 125 ± 38 | 132 ± 39 | 234 ± 82 | 122 ± 57 | 108 ± 51 | 3.86E+11 |
| Example 12 Ex 2 (87) ESO (13) | 89.6 ± 0.2 | 30.2 | 3696 ± 220 | 108 ± 10 | 107 ± 14 | 300 ± 33 | 93 ± 13 | 63 ± 17 | 5.08E+11 |
| Example 13 Ex 3 (87) ESO (13) | 90.3 ± 0.4 | 28.5 | 3643 ± 92 | 110 ± 3 | 110 ± 3 | 316 ± 12 | 93 ± 3 | 70 ± 5 | 4.55E+11 |
| Example 14 Ex. 4 (87) ESO (13) | 90.8 ± 0.3 | 31.7 | 3414 ± 203 | 108 ± 10 | 113 ± 10 | 311 ± 20 | 98 ± 10 | 74 ± 11 | 2.45E+12 |
| CS 4 DIDP (87) ESO (13) | 91.1 ± 0.3 | 28.1 | 2947 ± 288 | 114 ± 30 | 171 ± 16 | 243 ± 32 | 97 ± 43 | 18 ± 16 | 7.54E+12 |
| CS 5 TINTM (87) ESO (13) | 91.3 ± 0.4 | 30.6 | 2732 ± 319 | 110 ± 3 | 107 ± 13 | 229 ± 38 | 111 ± 7 | 91 ± 17 | 7.04E+12 |
| Example 15 Ex. 5 (87) ESO (13) | 89.2 ± 0.1 | 39.1 | 2373 ± 45 | 115 ± 3 | 113 ± 2 | 133 ± 7 | 89 ± 4 | 78 ± 4 | 2.39E+12 |
| CS 6 DIDP (87) ESO (13) | 93.1 ± 0.3 | 39.4 | 2308 ± 10 | 118 ± 23 | 249 ± 10 | 149 ± 2 | 37 ± 16 | 2 ± 0 | 8.63E+12 |
| CS 7 TOTM (87) ESO (13) | 95.0 ± 0.3 | 40.5 | 2356 ± 47 | 105 ± 3 | 108 ± 2 | 136 ± 4 | 101 ± 5 | 82 ± 2 | 4.61E+13 |

TABLE 4-continued

| Plasticizer Mixture† | Shore A Hardness ASTM D2240 | Tg (° C.) | TS (Unaged) - psi | TSR (%) after 113° C. Aging | TSR (%) after 136° C. Aging | TE (Unaged) - % | TER (%) after 113° C. Aging | TER (%) after 136° C. Aging | Vol Res |
|---|---|---|---|---|---|---|---|---|---|
| CS 8 ESO (100) | 92.9 ± 0.1 | 32.7 | 2464 ± 112 | 108 ± 4 | 233 ± 20 | 116 ± 2 | 98 ± 4 | 3 ± 0 | 7.72E+12 |

†= Weight percent for plasticizer components is shown in parenthesis.
Weight percent is based on total weight of the plasticizer

TABLE 5

| Plasticizer † Mixture | Hardness (Shore A) | TS (Unaged) - psi | TSR (%) after 136° C. Aging | TE (Unaged) - % | TER (%) after 136° C. Aging | Weight Retained (%) after 7 Days at 136° C. | Vol Res (Ohm cm) at 23° C. |
|---|---|---|---|---|---|---|---|
| Example 16 Ex 1 (87) ESO (13) | 94.7 ± 0.2 | 2507 ± 25 | 114 ± 5 | 147 ± 3 | 51 ± 7 | n/a | 1.44E+12 |
| Example 17 Ex 1 (65) ESO (35) | 93.0 ± 0.3 | 2352 ± 20 | 113 ± 2 | 150 ± 1 | 62 ± 4 | n/a | 1.45E+12 |
| Example 18 Ex 1 (43) ESO (57) | 93.1 ± 0.2 | 2533 ± 97 | 114 ± 6 | 148 ± 11 | 69 ± 10 | n/a | 3.27E+12 |
| CS 8 ESO (100) | 92.9 ± 0.1 | 2464 ± 112 | 233 ± 20 | 116 ± 2 | 3 ± 0 | 96.1 | 7.72E+12 |
| CS 9 DIDP (87) ESO (13) | 94.5 ± 0.4 | 2369 ± 78 | 252 ± 8 | 147 ± 9 | 1 ± 0 | n/a | 1.10E+13 |
| CS 10 TOTM (87) ESO (13) | 95.2 ± 0.2 | 2436 ± 150 | 110 ± 8 | 134 ± 1 | 87 ± 5 | n/a | 6.19E+13 |
| Example 19 Ex 6 (87) ESO (13) | 89.2 ± 1.0 | 3718 ± 257 | 121 ± 6 | 164 ± 27 | 87 ± 23 | 90.0 | 1.67E+12 |
| CS 11 TOTM (87) ESO (13) | 97.4 ± 0.2 | 4136 ± 69 | 86 ± 2 | 232 ± 98 | 96 ± 48 | 97.5 | 6.47E+13 |

† = Weight percent for plasticizer components is shown in parenthesis.
Weight percent is based on total weight of the plasticizer

TABLE 6

| Plasticizer Mixture† | TS (unaged)- psi | TSR (%) after 100° C. Oil Aging | TE (unaged)- % | TER (%) after 100° C. Oil Aging |
|---|---|---|---|---|
| Example 19 Ex 6 (87) ESO (13) | 3718 ± 257 | 112 ± 9 | 164 ± 27 | 71 ± 22 |
| CS 11 TOTM (87) ESO (13) | 4136 ± 69 | 137 ± 6 | 232 ± 98 | 6 ± 2 |

†= Weight percent for plasticizer components is shown in parenthesis.
Weight percent is based on total weight of the plasticizer

TABLE 7

Time to Make Dry Blends

| Plasticizer Mixture | Time to Make Dry Blend (minutes) |
|---|---|
| Example 19 Ex 6 (87) ESO (13) | 2.5 |
| CS 11 TOTM (87) ESO (13) | 4.5 |

TABLE 8

Results from Wire Extrusion

| Plasticizer † Mixture | Extruder RPM | Die Pressure (psi) | Surface Smoothness (γ in) | TS (unaged) - psi | TSR 136° C. | TSR (%) after 100° C. Oil Aging | TE (unaged) - % | TER 136° C. | TER (%) after 100° C. Oil Aging |
|---|---|---|---|---|---|---|---|---|---|
| Example 19 Ex 6 (87) ESO (13) | 40 | 2150 | 39 ± 7 | 2334 ± 45 | 219 ± 4 | 176 ± 11 | 96 ± 3 | 96 ± 6 | 40 ± 4 |
| CS 11 TOTM (87) ESO (13) | 14 | 1820 | 82 ± 17 | 2368 ± 27 | 143 ± 2 | 168 ± 3 | 63 ± 5 | 122 ± 8 | 3 ± 1 |

† = Weight percent for plasticizer components is shown in parenthesis.
Weight percent is based on total weight of the plasticizer

TABLE 9

| Plasticizer † Mixture | Time for Complete Absorption of Plasticizer (min) | Hardness (Shore D) | Hardness (Shore A) | TS (Unaged) - psi | TSR (%) after 136° C. Aging | TE (Unaged) - % | TER (%) after 136° C. Aging | Weight Retained (%) after 7 Days at 136° C. | Spew 136° C. | Vol Res (Ohm cm) at 23° C. |
|---|---|---|---|---|---|---|---|---|---|---|
| Example 20 Ex 6 (50) ESO (50) | n/a | 35.5 ± 0.4 | 86.7 ± 0.3 | 3373 ± 342 | 154 ± 19 | 221 ± 40 | 66 ± 13 | 93.2 | None | 4.60E+14 |
| Example 21 Ex 6A (50) ESO (50) | n/a | 38.8 ± 0.2 | 88.4 ± 0.2 | 3979 ± 140 | 108 ± 2 | 276 ± 6 | 78 ± 1 | 94.2 | None | 6.47E+15 |
| Example 22 Ex 6B (50) ESO (50) | n/a | 38.2 ± 0.3 | 88.9 ± 0.4 | 3606 ± 63 | 103 ± 2 | 256 ± 2 | 88 ± 2 | 98.0 | None | 3.00E+15 |
| Example 23 Ex 6C (50) ESO (50) | n/a | 39.9 ± 0.3 | 92.5 ± 0.4 | 3456 ± 109 | 104 ± 7 | 264 ± 8 | 81 ± 5 | 93.3 | None | 7.10E+15 |
| Example 24 Ex 6D (50) ESO (50) | n/a | 45.0 ± 0.5 | 94.5 ± 0.3 | 3925 ± 120 | 106 ± 1 | 258 ± 6 | 88 ± 1 | 98.5 | None | 5.89E+15 |
| Example 25 Ex 6 (100) | 4 | 35.4 ± 0.1 | 89.7 ± 0.5 | 3529 ± 326 | 116 ± 5 | 310 ± 31 | 44 ± 9 | 82.4 | None | 3.03E+13 |
| Example 26 Ex 6A (100) | 4 | 34.8 ± 0.7 | 90.3 ± 0.3 | 3645 ± 129 | 114 ± 6 | 322 ± 16 | 77 ± 10 | 89.8 | None | 6.09E+14 |
| Example 27 Ex 6B (100) | 6 | 38.6 ± 0.4 | 94.1 ± 0.3 | 3287 ± 390 | 101 ± 13 | 281 ± 60 | 93 ± 22 | 93.7 | None | 3.38E+14 |
| Example 28 Ex 6C (100) | 8 | 39.4 ± 0.3 | 93.4 ± 0.6 | 3249 ± 353 | 97 ± 8 | 292 ± 51 | 89 ± 17 | 95.0 | None | 1.48E+15 |
| Example 29 Ex 6D (100) | 6 | 39.6 ± 0.2 | 93.7 ± 0.4 | 3296 ± 130 | 102 ± 8 | 281 ± 18 | 101 ± 7 | 96.3 | None | 6.53E+14 |
| CS 12 TOTM (100) | 6 | 36.7 ± 0.7 | 91.0 ± 0.2 | 2886 ± 270 | 120 ± 28 | 250 ± 20 | 98 ± 37 | 97.1 | None | 8.21E+15 |

† = Weight percent for plasticizer components is shown in parenthesis.
Weight percent is based on total weight of the plasticizer The compositions of the Examples 7-29 exhibit properties that are similar to, or better than, those obtained with the comparative samples. Oil resistance at elevated temperature is substantially improved through the use of APE in the plasticizer composition. Absorption of plasticizer composition comprising APE in PVC, to make a dry blend, is much faster than the comparative trimellitate based plasticizer composition. The composition comprising APE resulted in a smooth extruded coating on wire with excellent properties.

Although epoxidized soybean oil is soluble in PVC and results in an acceptably low Shore A hardness, heat aging at 136° C. results in almost a complete loss in tensile elongation, making this composition unsuitable for high temperature applications.

Increasing the amount of ESO in the plasticizer mixture yields (i) lower hardness (i.e., greater plasticization efficiency), (ii) higher volume resistivity, and (iii) better retention of tensile elongation after heat aging of the composition.

It is specifically intended that the present disclosure not be limited to the embodiments and illustrations contained herein, but include modified forms of those embodiments including portions of the embodiments and combinations of elements of different embodiments as come within the scope of the following claims.

The invention claimed is:
1. A coated conductor comprising:
a conductor; and
a phthalate-free coating on the conductor, the phthalate-free coating comprising a polymeric composition comprising a vinyl chloride resin and a phthalate-free plasticizer composition comprising
an acetylated polyglyceride fatty acid ester consisting of
(i) a glycerol oligomer with two or more glycerol units linked by way of an ether bond and at least one fatty acid component, the fatty acid component composed of an aliphatic chain having 4 to 22 carbon atoms, and (ii) at least one acetyl group, wherein the acetylated polyglyceride fatty acid ester has a hydroxyl number of 0 and a solution temperature from 140° C. to 200° C., and an epoxidized fatty acid ester;

wherein the glycerol oligomer is a tetraglycerol and the fatty acid component is lauric acid.

2. The coated conductor of claim 1 wherein the plasticizer composition comprises from about 10 wt % to about 90 wt % of the acetylated polyglyceride fatty acid ester.

3. The coated conductor of claim 1 wherein the vinyl chloride resin is polyvinyl chloride.

4. The coated conductor of claim 1, wherein the coating comprises a heat stabilizer.

5. The coated conductor of claim 1 wherein the plasticizer composition comprises a third plasticizer.

6. The coated conductor of claim 1, wherein the polymeric composition has a tensile elongation retention greater than 30% after 168 hours heat aging at 136° C. as measured in accordance with ASTM D638.

7. The coated conductor of claim 1, wherein the polymeric composition comprises from 20 wt % to 80 wt % of the vinyl chloride resin and from 20 wt % to 80 wt % of the plasticizer composition.

8. The coated conductor of claim 1, wherein the acetylated polyglyceride fatty acid ester has a molecular weight from 500 to 2,000 g/mol and a viscosity from 100 mPa·s to 3,000 mPa·s at 25° C.

9. The coated conductor of claim 1, wherein the plasticizer composition consists of the acetylated polyglyceride fatty acid ester and the epoxidized fatty acid ester.

10. A coated conductor comprising:

a conductor; and a phthalate-free coating on the conductor, the phthalate-free coating comprising a polymeric composition comprising from 20 wt % to 80 wt % of a vinyl chloride resin and from 20 wt % to 80 wt % of a plasticizer composition consisting of:

an acetylated polyglyceride fatty acid ester consisting of (i) a glycerol oligomer with two or more glycerol units linked by way of an ether bond and at least one fatty acid component, the fatty acid component composed of an aliphatic chain having 4 to 22 carbon atoms, and (ii) at least one acetyl group, wherein the acetylated polyglyceride fatty acid ester has a hydroxyl number of 0 and a solution temperature from 140° C. to 200° C., and an epoxidized soybean oil, wherein the glycerol oligomer is a tetraglycerol and the fatty acid component is lauric acid.

11. The coated conductor of claim 10, wherein the polymeric composition has a tensile elongation retention greater than 30% after 168 hours heat aging at 136° C. as measured in accordance with ASTM D638.

12. The coated conductor of claim 10, wherein the phthalate-free coating has a thickness from 0.01 inches to 0.2 inches.

13. The coated conductor of claim 10, wherein the acetylated polyglyceride fatty acid ester has a molecular weight from 500 to 2,000 g/mol and a viscosity from 100 mPa·s to 3,000 mPa·s at 25° C.

14. The coated conductor of claim 10, wherein the plasticizer composition consists of from 10 wt % to 90 wt % of the acetylated polyglyceride fatty acid ester and from 10 wt % to 90 wt % of the epoxidized soybean oil.

15. The coated conductor of claim 10, wherein the conductor consists of a metal wire.

16. The coated conductor of claim 10, wherein the conductor comprises an optical fiber.

* * * * *